United States Patent
Gao et al.

(10) Patent No.: US 10,335,777 B2
(45) Date of Patent: Jul. 2, 2019

(54) ZSM-5 CATALYST

(71) Applicant: BASF Corporation, Florham Park, NJ (US)

(72) Inventors: Xingtao Gao, Holmdel, NJ (US); Christopher R. Castellano, Ringoes, NJ (US); Brendan Patrick Dowd, Brick, NJ (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 15/557,786

(22) PCT Filed: Apr. 8, 2016

(86) PCT No.: PCT/US2016/026608
§ 371 (c)(1),
(2) Date: Sep. 12, 2017

(87) PCT Pub. No.: WO2016/164698
PCT Pub. Date: Oct. 13, 2016

(65) Prior Publication Data
US 2018/0071723 A1    Mar. 15, 2018

Related U.S. Application Data (60) Provisional application No. 62/145,170, filed on Apr. 9, 2015.

(51) Int. Cl.
| | | |
|---|---|---|
| *B01J 29/40* | (2006.01) | |
| *C01B 39/38* | (2006.01) | |
| *C01B 39/40* | (2006.01) | |
| *B01J 35/08* | (2006.01) | |
| *B01J 35/00* | (2006.01) | |
| *B01J 35/10* | (2006.01) | |
| *B01J 37/00* | (2006.01) | |
| *B01J 37/02* | (2006.01) | |
| *B01J 21/12* | (2006.01) | |
| *B01J 37/08* | (2006.01) | |
| *C07C 2/76* | (2006.01) | |
| *B01J 35/02* | (2006.01) | |

(52) U.S. Cl.
CPC ............. *B01J 29/40* (2013.01); *B01J 21/12* (2013.01); *B01J 35/002* (2013.01); *B01J 35/0006* (2013.01); *B01J 35/0026* (2013.01); *B01J 35/08* (2013.01); *B01J 35/1019* (2013.01); *B01J 37/0018* (2013.01); *B01J 37/0045* (2013.01); *B01J 37/0072* (2013.01); *B01J 37/0203* (2013.01); *B01J 37/0221* (2013.01); *B01J 37/08* (2013.01); *C01B 39/38* (2013.01); *C01B 39/40* (2013.01); *C07C 2/76* (2013.01); *B01J 35/023* (2013.01); *B01J 2229/60* (2013.01); *B01J 2229/62* (2013.01); *C01P 2004/32* (2013.01); *C01P 2006/21* (2013.01); *C07C 2521/12* (2013.01); *C07C 2529/40* (2013.01)

(58) Field of Classification Search
CPC ..... C01B 39/38; C01B 39/40; C01P 2004/32; C01P 2006/21; B01J 29/40; B01J 37/0045; B01J 2229/60; B01J 2229/62
See application file for complete search history.

(56) References Cited

U.S. PATENT DOCUMENTS

| | | | |
|---|---|---|---|
| 4,476,239 A * | 10/1984 | Chiang et al. ......... | B01J 29/084 502/68 |
| 4,493,902 A | 1/1985 | Brown et al. | |
| 4,631,262 A | 12/1986 | Altomare | |
| 5,672,331 A | 9/1997 | Verduijn | |
| 5,958,818 A | 9/1999 | Demmel et al. | |
| 5,993,642 A | 11/1999 | Mohr et al. | |
| 5,994,603 A | 11/1999 | Mohr et al. | |
| 6,039,864 A | 3/2000 | Mohr et al. | |
| 6,040,259 A | 3/2000 | Mohr et al. | |
| 6,111,157 A | 8/2000 | Hendriksen et al. | |
| 6,150,293 A | 11/2000 | Verduijn et al. | |
| 6,198,013 B1 | 3/2001 | Mohr et al. | |
| 6,699,811 B1 | 3/2004 | Mohr et al. | |

(Continued)

FOREIGN PATENT DOCUMENTS

| | | |
|---|---|---|
| CN | 102372286 | 3/2012 |
| CN | 102583434 | 7/2012 |

(Continued)

OTHER PUBLICATIONS

International Search Report and Written Opinion of the International Search Authority for International Application No. PCT/US2016/26608 dated Jul. 12, 2016, 10 pages.

(Continued)

*Primary Examiner* — David M Brunsman
(74) *Attorney, Agent, or Firm* — Lowenstein Sandler LLP (57) ABSTRACT

Disclosed in certain embodiments are ZSM-5 zeolite microspheres. Disclosed in certain embodiments is a method of forming ZSM-5 zeolite microspheres including: 1) shaping a mixture into microspheres where the mixture includes a silica material and of particulates selected from at least one high-density material with an absolute bulk density of at least 0.3 g/cc, ZSM-5 zeolite crystals, and combinations thereof; 2) calcining the microspheres; and 3) reacting and subsequently heating the microspheres with at least one alkali solution to form ZSM-5 zeolite in-situ on the microspheres, where the ZSM-5 zeolite microspheres contain substantially no clay or calcined clay material.

20 Claims, 3 Drawing Sheets

(56) References Cited

U.S. PATENT DOCUMENTS

| | | | |
|---|---|---|---|
| 6,831,203 B1 | 12/2004 | Mohr et al. | |
| 7,601,330 B2 | 10/2009 | Wang et al. | |
| 8,398,955 B2 | 3/2013 | Lai et al. | |
| 2010/0160527 A1 | 6/2010 | Royer et al. | |
| 2013/0225397 A1 | 8/2013 | Ma et al. | |
| 2018/0071723 A1* | 3/2018 | Gao | B01J 35/002 |

FOREIGN PATENT DOCUMENTS

| | | |
|---|---|---|
| CN | 103785449 | 5/2014 |
| EP | 0156595 | 12/1992 |
| WO | 0066263 | 11/2000 |

OTHER PUBLICATIONS

Feng et al., "In-situ Synthesis of ZSM-5 on Silica Gel and studies on its Catalytic Activity", Journal of Fuel Chemistry and Technology, vol. 36, No. 2, pp. 144-150, Dec. 2008, 8 pages.

Extended European Search Report for Application No. 16 77 7339 dated Dec. 5, 2018, 12 pages.

\* cited by examiner

ZSM-5 CATALYST

CROSS-REFERENCE TO RELATED APPLICATIONS

This application is a national stage entry under 35 U.S.C. § 371 of International Application No. PCT/US2016/026608, filed on Apr. 8, 2016, which claims the benefit of priority of U.S. Provisional Patent Application Ser. No. 62/145,170, filed on Apr. 9, 2015, the disclosures of which are hereby incorporated by reference herein in their entireties.

TECHNICAL FIELD

The present disclosure is directed towards synthesis of a ZSM-5 catalyst having high zeolite content and integrity, and its use thereof.

BACKGROUND

Zeolite is widely used as a catalyst, an adsorbent, a molecular sieve, an ion exchanger or the like because it has a peculiar three-dimensional crystal structure of aluminosilicate, and has large pore and excellent ion-exchange performance compared to other aluminosilicate crystals. The use of natural zeolite is limited because of its structural restrictions, but the use of synthetic zeolite is gradually enlarged. In order to expand the use of zeolite, it is required to arbitrarily control the crystal size, particle size distribution, and form of zeolite to efficiently synthesize zeolite.

ZSM-5 zeolite forms three-dimensional pores defined by 10 tetrahedron rings, and its size is equal to that of zeolite A or is in the middle between zeolite X and zeolite Y. Further, ZSM-5 zeolite is a kind of pentasil zeolite which is a shape-selective catalyst exhibiting peculiar adsorption and diffusion characteristics, and generally has high thermal stability and has hydrophobicity because it has high ratio of $SiO_2/Al_2O_3$ (silica/alumina). Further, ZSM-5 zeolite has both Lewis and Brønsted acid sites. In particular, ZSM-5 zeolite is used to directly obtain gasoline fraction having a high octane number from methanol by an MTG process, and is known to have excellent selectivity of gasoline fraction.

After ZSM-5 having a high content of silica was first developed by Mobil™ Oil Corporation in the early 1970's, research into this material has been variously made due to peculiar catalytic activity and shape selectivity resulting from the molecular sieve effect of this material. Unlike aluminosilicate zeolite, various kinds of organic materials have been used as structure inducing substances for forming a structure to prepare ZSM-5.

The conventional ZSM-5 catalysts are prepared by using binder material to form shaped-bodies, such as using spray-drying or extrusion to obtain the final formed catalyst, i.e. microspheres or extrudates, respectively. Due to the requirements on binding strength and other components, limited amount of zeolite crystals can be incorporated in the shaped catalyst form.

In the preparation of ZSM-5 zeolite microspheres, typically microspheres are formed first, and then the zeolite component crystals are combined in a separate step with the microspheres. In another technique, i.e., in situ crystallization technique, microspheres are first formed then the zeolite component is crystallized in situ within microspheres, to provide microspheres containing zeolite component.

In many catalytic processes, such as fluid catalytic cracking (FCC) processes, useful zeolite microspheres must be attrition-resistant as well as sufficiently porous. Generally, one of these qualities is achieved at the expense of the other. For example, as a microsphere of given chemical composition is formulated to be highly porous, the hardness usually decreases. Generally, in microsphere additives that contain higher than 25% ZSM-5 levels, the attrition resistance of the microspheres becomes an issue.

Kaolin alone or with a zeolitic molecular sieve can form coherent bodies such as microspheres which, when calcined, are further hardened. Kaolin is used as an ingredient for making microspheres for both economic and efficiency reasons. However, certain conversion processes, such as the conversion of methane to benzene performs poorly in the presence of kaolin microspheres, due to the fact that such microspheres are not inert to the conversion.

Further, for conventional ZSM-5 catalysts, seeds are often required to induce crystallization to form ZSM-5 zeolite within the microspheres. The ZSM-5 seeds incur additional cost in the zeolite synthesis by the in situ method.

There have been numerous attempts to either reduce the use of kaolin microspheres, or minimize ZSM-5 seeds in the in situ production of ZSM-5 catalysts.

Several ExxonMobil® U.S. patents (U.S. Pat. Nos. 6,831,203; 6,699,811; 6,198,013; 6,150,293; 6,111,157; 6,040,259; 6,039,864; 5,993,642) have shown that the first zeolite crystals can be coated and bound by the second inter-grown zeolite crystals crystallized from silica binder that binds the first zeolite crystals. The final zeolite catalyst (including both first and second zeolite crystals) contains less than 5% non-zeolite binder. The second zeolite as binder includes MFI crystals (U.S. Pat. No. 6,150,293). U.S. Pat. No. 6,150,293 teaches a preparation method for making zeolite bound by MFI structure type zeolite.

Chinese patent application CN 103785449A to Yuanyuan discloses a preparation method of no binder ZSM-5 catalyst consisting of mixing ZSM-5 crystals with solid silica fine particles of less than 10 wt. % and promoters of phosphorus and lanthanum elements in ranges of 0.1-10 wt. % and 0.01-5 wt. %, respectively. The mixture was extruded into extrudates that are further crystallized in a steam environment containing organic template molecules in gas phase. The fine silica particles were then converted to in-situ ZSM-5 nanoparticles (<1 µm) on top of existing large ZSM-5 crystals to provide the extrudates with mechanical strength.

US 2013/0225397 to Ma teaches mixing ZSM-5, 0.1-20 wt. % of an oxide or hydroxide, an aluminum compound and silica, molding and drying to obtain a molded catalyst precursor mix I, then crystallizing the mix I at 100-200° C. in water vapor or template vapor, drying and calcining the catalyst precursor to obtain a binderless molecular sieve catalyst.

U.S. Pat. No. 5,672,331 to Verduijn teaches MFI zeolite crystals of uniform and controllable size is produced by mixing a source of particulate silica, seeds of an MFI zeolite in the form of a colloidal suspension, an organic structure directing agent, and a source of fluorine or an alkali metal to form an aqueous synthesis mixture, and allowing the synthesis mixture to crystallize.

U.S. Pat. No. 7,601,330 to Wang teaches a process for producing a binder-free homogeneously crystallized and shaped ZSM-5 zeolite crystals comprising: mixing, a silica source, an aluminum source, ZSM-5 seeds, and an extrusion aid together with a silica sol or water glass then converting to binder-free ZSM-5 shaped zeolites by vapor-solid phase crystallization with organic amine and water vapor.

CN 102372286 to Wang teaches a method for the synthesis of small crystal ZSM-5 zeolite, comprising: mixing a directing agent of silica source that is formed by spray-drying having a resulting particle size of 10-200 am, with a base, a templating agent, and water and mix to obtain a raw material mixture, and the mixture was heated and dried to obtain crystal ZSM-5 zeolite.

U.S. Pat. No. 8,398,955 to Lai teaches a method of preparing a molecular sieve composition having at least one crystalline molecular sieve comprising the steps of: providing a reaction mixture of at least one source of ions of tetravalent element Y such as silicon or germanium, at least one source of alkali metal hydroxide, water, optionally at least one seed crystal, and optionally at least one source of ions of trivalent element X, wherein said reaction mixture is substantially free of a crystalline molecular sieve, extruding said reaction mixture to form a pre-formed extrudate; and crystallizing said pre-formed extrudate in a liquid medium comprising water under liquid phase conditions to form said molecular sieve composition having the crystalline molecular sieve.

CN 102583434 to Li teaches a ZSM-5 zeolite microsphere preparation of the following steps: mixing siloxanes and alcohol, an aluminum source, sodium hydroxide, organic amines, TEOS, and water; wash, heat then calcine to obtain ZSM-5 zeolite microspheres.

However, the mentioned prior art either require ZSM-5 seeds, or express no attrition resistance rate or high zeolite content for the resulted zeolitic microsphere. Accordingly it would be desirable to produce high attrition resistant ZSM-5 zeolite catalyst in-situ with substantially no clay base microspheres and/or ZSM-5.

SUMMARY OF THE DISCLOSURE

The following presents a simplified summary of various aspects of the present disclosure in order to provide a basic understanding of such aspects. This summary is not an extensive overview of the disclosure. It is intended to neither identify key or critical elements of the disclosure, nor delineate any scope of the particular embodiments of the disclosure or any scope of the claims. Its sole purpose is to present some concepts of the disclosure in a simplified form as a prelude to the more detailed description that is presented later.

In one aspect of the present disclosure, ZSM-5 zeolite microspheres are formed by 1) shaping a mixture comprising a silica material, and particulates selected from the group consisting of high density particle with an absolute bulk density of at least 0.3 g/cc, ZSM-5 zeolite crystals, and mixtures thereof, into microspheres; 2) calcining the microspheres, such that the calcined microspheres have an absolute bulk density of at least 0.5 g/cc; and 3) reacting and subsequently heating the calcined microsphere with an alkali solution, and optionally an organic template compound, to form in-situ ZSM-5 zeolite microspheres, wherein the zeolite containing microspheres contain substantially no clay or calcined clay material, and has a ZSM-5 zeolite content of at least 70 wt. % of the microsphere.

In one embodiment, the ZSM-5 zeolite containing microspheres contain small inter-bound/inter-growth ZSM-5 crystals to provide excellent mechanical stability and attrition resistance.

In another aspect of the present disclosure, a method includes hydrocarbon conversion reactions, such as converting methane to benzene using the ZSM-5 zeolite containing microspheres.

BRIEF DESCRIPTION OF THE DRAWINGS

The present disclosure is illustrated by way of example, and not by way of limitation, in the figures of the accompanying drawings, in which.

DETAILED DESCRIPTION

In one aspect of the present disclosure, ZSM-5 microspheres are formed by 1) shaping a feed mixture comprising a) a silica material selected from the group consisting of colloid silica, silica sol, fumed silica, dense $SiO_2$ particles, precipitated silica, any amorphous silica doped with Al, sodium silicate and mixtures thereof; and b) particulates selected from the group consisting of at least one high density particles with absolute bulk density (ABD) of at least 0.3 g/cc, ZSM-5 zeolite crystals, and mixtures thereof, into microspheres; 2) calcining the microspheres, such that the calcined microspheres have an absolute bulk density of at least 0.5 g/cc; and 3) reacting the calcined microspheres with an aqueous alkali solution, and optionally an organic template compound, to form ZSM-5 in-situ on the calcined microspheres.

The ZSM-5 zeolite containing microspheres are substantially free of clay (e.g., kaolin clay) or calcined clay material, that is, the microspheres are substantially made from materials other than clay, and only a minor amount of clay, in the form of reactive kaolin and in the amounts of less than 8 wt. %, preferably less than 6 wt. % is added in the feed mixture and/or the reactive mixture as a consumable aluminum source to provide aluminum nutrient for the zeolite formation. In one embodiment, no more than 8 wt. % of clay or calcined clay is present in the feed mixture or in the in the ZSM-5 zeolite microspheres. The minor amount of consumable clay is to be completed consumed for zeolite formation, thus leaving no trace of clay material in the final zeolitic ZSM-5 microspheres. ZSM-5 zeolite containing microspheres that contain substantial clay material as the main structure component, even after calcination, may contain residual spinel or reactive kaolin that can interfere with the conversion process of methane to benzene. Thus it is desirable to use none or minimal amounts of clay material for forming the microspheres prior to crystallization. Typical clay materials include kaolinite, montmorillonite-smectite, illite, chlorite, varve and quick clay.

In one embodiment, for structuring the microspheres, a high-density material (e.g., high density particles) of a density over 0.3 cc/g, preferably over 0.6 cc/g are used instead. The high-density material forms a core onto which the silica material deposits upon as a shell (e.g., the silica material coats the at least one high-density material), to form a "core-shell" configuration during the shaping (i.e. spray-drying) prior to calcination. In one embodiment, the high-density material has a particle size of about 1 to 150 microns, preferably 5 to 100 microns, and more preferably 10 to 80 microns. The high-density material may be selected from the group consisting of α-$Al_2O_3$ (alpha alumina), precipitated silica, steatite, minerals, silicates, aluminates, amorphous silica (e.g., amorphous silica oxide), an aluminum hydroxide, an aluminum oxide, and mixtures thereof. The amount of high-density material is in the range from 5 to 90 wt. %, preferably from 10 to 75%, and more preferably 20 to 50 wt. % of the feed mixture. In one embodiment, the feed mixture contains substantially no ZSM-5 seeds (e.g., ZSM-5 seedings, ZSM-5 seed crystals).

In another embodiment, ZSM-5 crystals may be used as the main structuring component, replacing the high-density material. An addition of ZSM-5 crystals to the mixture is not essential for initiating the in-situ ZSM-5 crystal growth for making the ZSM-5 zeolite containing microspheres. In one embodiment, the ZSM-5 crystals are be present in the mixture on the dry weight basis from 10 to 70 wt. %, preferably 20 to 50 wt. % of the feed mixture.

The inclusion of silica material, however, increases the overall reactive $SiO_2/Al_2O_3$ ratio, resulting in an increased level of crystallized ZSM-5. In one embodiment, the silica material is present in the amount of 10 to 90 wt. %, preferably 15 to 60 wt. % and more preferably 20 to 50 wt. % of the feed mixture. In another embodiment, the silica material is present in the amount of 20 to 95% of the feed mixture.

In one embodiment, the microspheres are made by adding water to the feed mixture to form an aqueous slurry and spray-drying the slurry. The amount of water applied to the feed mixture is about 2 to 60 wt. %, preferably 5 to 50 wt. %, and more preferably 10 to 40 wt. %. To help the formation of microspheres, a spray-drying aid may be added to the feed mixture. The spray-drying aid may be selected from the group consisting of ammonium citrate, sodium hexametaphosphate, ammonium tartrate, ammonium chloride, monoethylamine, ammonium oxalate, ammonium polyacrylate, carboxymethyl cellulose, polyvinyl alcohol and tetrasodium phosphate. The spray-drying aid is used in the amount of 0.1 to 5 wt. %, preferably 0.2 to 3 wt. %, and more preferably 0.5 to 2.5 wt. % of the shaped mixture. In another embodiment, a pore forming agent may be used for the formation of additional macro- and meso-pores in the microspheres. The pore forming agent may be selected from the group of starch and surfactants. In another embodiment, an acid washing step may be needed after spray-drying if the microspheres contain sodium level higher than 1 wt. % Na2O, particularly higher than 2 wt. % Na2O when sodium silicate is used in the feed mixture. The microspheres are calcined before crystallization at a temperature of from 120 to 1200° C., preferably 600 to 1000° C. for 0.5 to 10 hours, preferably for 1 to 5 hours, and more preferably from 2 to 4 hours. Typically, the calcined precursor microspheres have a BET surface area of less than 200 m2/g and an absolute bulk density of at least 0.5 cc/g.

The calcined microspheres are then reacted with a solution of an alkali metal compound (e.g., an alkali solution) and optionally an organic template compound to form a reactive mixture. The alkali metal compound is selected from the group consisting of sodium hydroxide, sodium silicates or a sodium containing seed solution used for forming zeolite Y, and mixtures thereof. The at least one alkali solution may be present in the amount of 1 to 20 wt. % of the reactive mixture.

The reactive mixture also includes about 30 to 90 wt. % of water, preferably 40% to 85 wt. % of water, and more preferably 50 to 75 wt. % of water. The reactive mixture may further include an aluminum source to facilitate in-situ crystallization of ZSM-5 zeolite, such that the ZSM-5 zeolite containing microspheres achieve a $SiO_2/Al_2O_3$ molar ratio of 20 to 100, preferably 25 to 80.

The alkali solution may include zeolite Y seed. In one embodiment, a zeolite Y seed solution may be obtained by processes as disclosed in U.S. Pat. No. 4,493,902 and U.S. Pat. No. 4,631,262, the entire contents of which are herein incorporated by reference. As disclosed in U.S. Pat. No. 4,631,262, appropriate quantities of sodium silicate, sodium aluminate and sodium hydroxide are mixed, preferably in a controlled manner, hereinafter described, heating the resulting mixture for a time sufficient for the seeds to mature but insufficient for cloudiness to occur, and thereafter adding to the matured solution a portion of the sodium silicate reactant. The sodium silicate added to the matured seed solution is preferably at ambient temperature when it is added to the solution. The amount of sodium silicate solution added to the solution of matured clear seeds is effective to result in a seed solution, which will maintain its clarity when aged for 48 hours or longer (without cooling). In effect, enrichment of a clear solution of matured seeds with sodium silicate functions to quench the undesirable reaction(s) that may take place and which would result in undesired cloudiness. The seed solution is amorphous and does not exhibit any detectable crystallinity by x-ray diffraction (XRD). The amount of zeolite Y seed solution used for the reactive mixture is about 1 to 30 wt. %, preferably 3 to 20 wt. %, and most preferably 5 to 15 wt. % of the reactive mixture.

In another embodiment, the method of producing ZSM-5 zeolite microspheres does not require a zeolite Y seed solution, and can produce similarly desirable ZSM-5 zeolite microspheres with a solution containing solely alkali silicate instead. In one embodiment, the alkali silicate solution is a solution of sodium silicate that has a ratio of 3.22 $SiO_2$ to $Na_2O$. In another embodiment, the sodium silicate solution is marketed under N-brand by Q.P. Corp. In another embodiment, the amount of alkali silicate solution for the reactive mixture is about 1 to 30 wt. %, preferably 3 to 20 wt. %, and most preferably 5 to 15 wt. % of the reactive mixture.

In another embodiment, the method of producing ZSM-5 zeolite microspheres does not require either a zeolite Y seed solution or an organic template, and can produce similarly desirable ZSM-5 zeolite microspheres with a solution containing solely alkali hydroxide (e.g., the alkali solution) instead. The alkali hydroxide in the reactive mixture is either an alkali oxide or a solid hydroxide dissolving in the reactive mixture, or a highly concentrated alkali hydroxide solution, or ammonium hydroxide, or a mixture thereof. The amount of alkali hydroxide useful for the reactive mixture is about 0.1 to 30 wt. %, preferably 1 to 20 wt. %, and most preferably 2 to 15 wt. % of the reactive mixture.

The optional organic template compound is selected from the group consisting of tetramethylammonium chloride, tetrapropylammonium bromide, tetrapropylammonium hydroxide, tri-n-propylamine, and n-propyl bromide, and other quaternary ammonium cations. The template compound, if used, is present in the amount of 0.5 to 20 wt. %, preferably 1.0 to 15 wt. %, and most preferably 1.5 to 13 wt. % of the reactive mixture.

Alternatively, the microspheres may be impregnated with the organic template compound prior their addition to the reactive mixture. The impregnation is essentially an incubation of the microspheres with a solution that contains the organic template compound for a period of half hour to 5 hours at a temperature in the range of 20 to 100° C. The wet and impregnated microspheres are then dried at 80° C. for 16 hours prior to their addition to the reactive mixture for crystallization.

The aluminum source is selected from the group consisting of an aluminum salt, an aluminum hydroxide, aluminate, an aluminum oxide and a metakaolin (MetaMax®). The reactive mixture preferably has an aluminum source in the amount of 0.01 to 5 wt. %, preferably 0.1 to 4 wt. %, and most preferably 0.4 to 3 wt. %. It must be noted that the metakaolin, whether it exists in microspheres or separately in reactive mixture, if applied, converts entirely to zeolite and forms no part of the microsphere structure.

The crystallization within the reactive mixture takes place at a temperature from 140 to 200° C., preferably 150 to 190° C., for a period time from 0.1 hours to 100 hours, preferably from 1 hour to 50 hours. In another embodiment, the reactive mixture undergoes crystallization to form the ZSM-5 zeolite at a temperature from 140 to 200° C. for a period of time from 5 to 100 hours. The agitation rate of the crystallization mixture is sufficient to well mix all components but not too high to break the particles by the stirrer or other mixing apparatus. The agitation rate, depending on the size of the reactor, can be in the range of 20 to 400 rpm, preferably 80 to 300 rpm.

After the crystallization reaction is completed, the product is filtered from the mother liquor and either washed with water, and/or calcined at a temperature from 300 to 750° C., preferably 500 to 650° C., for a period time from 0.5 hours to 30 hours, preferably from 1 hours to 10 hours. If an organic template compound is used, the template compound in the mother liquor as well as in zeolite material after crystallization process may be recycled for re-use.

The produced ZSM-5 zeolite microsphere contains small inter-bound/inter-growth ZSM-5 crystals with an average crystal size measured by x-ray diffraction of less than 800 Å, preferably less than 700 Å, and more preferably less than 600 Å. The air jet attrition rate (AJAR) of the produced ZSM-5 zeolite microsphere is below 5.0, preferably below 4.0, most preferably below 3.0, which is suitable for fluidized bed catalytic reactions. The $SiO_2/Al_2O_3$ molar ratio (SAR) of the ZSM-5 crystals is in the range from 20 to 100, preferably from 25 to 80. The ZSM-5 zeolite containing microspheres have a size of about 10 to 250 microns, preferably 25 to 200 microns, and more preferably 50 to 150 microns.

The resulting ZSM-5 zeolite microspheres, after removing sodium and the optional template compound, is useful as a catalyst, a component of a catalyst or an intermediate of a catalyst for hydrocarbon conversion processes. The sodium cations within the microspheres can be removed by ammonium or acid ion-exchange process, as known to the art. If the ZSM-5 material contains organic template molecules, these molecules can be removed by calcination or other chemical means such as extraction using solvents. The ZSM-5 microspheres prepared by the present disclosure can be further treated with phosphorous, including phosphorous acid or ammonium phosphorous salts, to be useful as additives for petrochemical FCC process.

ILLUSTRATIVE EXAMPLES OF GENERAL EMBODIMENTS

Example 1

The purpose of this example is to illustrate that in-situ ZSM-5 crystallization provides strong integrity to bind existing ZSM-5 crystals and achieve very high ZSM-5 content and attrition resistance for the microspheres.

The microspheres were made by a pilot plant Bayliss spray dryer with nozzle-type atomizer from a feed mixture: 6440 parts of ZSM-5 crystals at 37% solids, 5930 parts of Nalco 1144 (colloid silica) at 40% solids, 118 parts of ammonium citrate and 472 parts of water. The zsm-5 crystals with a SAR of 28 and average crystal size determined by XRD at 1158 Å were milled down to that 90% of the particles were less than 3 micron. After spray-drying, the microspheres, designated as MS-1, were calcined at 1800° F. (982.2° C.) for 2 hrs. MS-1 has an ABD of 0.8 cc/g.

The reaction mixture for in situ crystallization was composed of 6.84 g TPA Br, 107.6 g DI water, 3.22 g Meta-Max®, 17.56 g seeds solution and 55.0 g MS-1.

The seeds solution used has a composition listed in Table 1.

TABLE 1

| $Na_2O$, wt. % | $SiO_2$, wt. % | $Al_2O_3$, wt. % |
|---|---|---|
| 12.22 | 22.23 | 0.35 |

The reaction proceeded at about 180° C. under agitation of 300 rpm in an autoclave for 20 hours. The microspheres after the reaction were filtered from the mother liquor and then calcined at 600° C. for 2 hrs. The "as crystallized" microspheres were found to have 93% crystallinity by X-ray diffraction and a total BET surface area of 295 $m^2/g$. The air jet attrition rate (AJAR) was measured at 1.72 and attrition index of 13. The average crystal size measured by XRD is 605 Å.

Example 2

The starting microspheres of this example were MS-1 as Example 1. The reaction mixture for in situ crystallization was composed of 77.7 g TPA Br, 1172 g DI water, 36.6 g MetaMax®, 199.5 g seeds solution and 625.0 g MS-1. The reaction proceeded at about 180° C. under agitation of 200 rpm in an autoclave for 20 hours. The microspheres after the reaction were filtered from the mother liquor. The "as crystallized" microspheres were washed with water and then ion-exchanged with ammonium nitrate at pH 3 and calcined at 600° C. for 5 hrs. The material was further ion-exchanged with ammonium nitrate at pH 1.0 and calcined again at 600° C. for 2 hrs. The resulting H-ZSM-5 microspheres were found to have 93% crystallinity by x-ray diffraction and a total BET surface area of 340.3 $m^2/g$. The air jet attrition rate (AJAR) was measured at 1.44 and attrition index of 8. The average crystal size measured by XRD is 664 Å.

Example 3

The purpose of this example is to illustrate that in-situ ZSM-5 crystallization provides strong integrity to bind existing ZSM-5 crystals and other high-density particles with increased ZSM-5 content.

The microspheres were made by a pilot plant Bayliss spray dryer with a nozzle type atomizer from a feed mixture: 6500 parts of ZSM-5 at 36% solids, 2920 parts of Nalco 1144 at 40% solids, 1170 parts of $\alpha\text{-}Al_2O_3$ powder and 1170 parts of water. The ZSM-5 crystals with SAR of 28 in the feed mixture were milled down to that 90% of particles were less than 3 μm. The $\alpha\text{-}Al_2O_3$ powder has an average particle size of about 1 μm and an absolute bulk density of 0.66 cc/g. After spray-drying, the microspheres, designated as MS-2, were calcined at 1800° F. (982.2° C.) for 2 hrs. MS-2 has an ABD of 0.7 cc/g.

650 g MS-2 was pre-impregnated with 316.5 g 25.5 wt % TPA Br solution. The wet microspheres were then dried at 80° C. for 16 hours. The dried TPA Br pre-impregnated microspheres were mixed with 207.53 g seeds solution, 9.51 g MetaMax® and 1257 g deionized (DI) water. The reaction proceeded at about 180° C. under agitation in an autoclave for 20 hours. The microspheres after the reaction were filtered from the mother liquor and then calcined at 600° C. for 2 hrs. The "as crystallized" microspheres were found to have 73% crystallinity by x-ray diffraction and a total BET surface area of 225 m$^2$/g. The air jet attrition rate (AJAR) was measured at 1.56 and attrition index of 8. The average crystal size measured by XRD is 559 Å.

Example 4

The purpose of this example is to illustrate that in-situ crystallization can form in-situ ZSM-5 microspheres with high zeolite content and good attrition resistance from core-shell type silica microspheres without ZSM-5 crystals.

The microspheres were made by a pilot plant Bayliss spray dryer with a nozzle type atomizer from a feed mixture: 1000 parts of dense silica core, 1851 parts of Nalco 1144 (colloid silica) at 40% solids, 111 parts of ASP-200 kaolin powder and 1666 parts of water. The dense silica core has a diameter of 78 micron and a density of 0.79 cc/g. After spray-drying, the microspheres, designated as MS-3, were calcined at 1800° F. (982.2° C.) for 2 hours to convert ASP-200 kaolin in microspheres to metakaolin to provide Al nutrients for zeolite crystallization. MS-3 has an ABD of 0.5 cc/g.

The reaction mixture for in-situ crystallization was composed of 6.84 g TPA Br, 157.6 g DI water, 1.61 g Meta-Max®, 17.56 g seeds solution and 55.0 g MS-3. The reaction proceeded at about 180° C. under agitation of 300 rpm in an autoclave for 20 hours. The microspheres after the reaction were filtered from the mother liquor and then calcined at 600° C. for 2 hrs. The "as crystallized" microspheres were found to have 84% crystallinity by x-ray diffraction and a total BET surface area of 228.3 m$^2$/g. The air jet attrition rate (AJAR) was measured at 3.92 and attrition index of 29. The average crystal size measured by XRD is 721 Å.

Comparative Example 1

This comparative example illustrates that a reactive mixture for in-situ crystallization similar to conditions as taught by U.S. Pat. No. 6,150,293 formed in-situ ZSM-5 microspheres with low zeolite content and poor attrition resistance.

The starting microspheres of this example were MS-1 as described in Example 1. 2.53 g NaOH and 17.53 g aluminum sulfate Octadecahydrate were dissolved in 157.6 g DI water. 8.78 g TPA Br was dissolved in 96.73 g DI water in a separate container. The two solutions were mixed in an autoclave. 55 g MS-1 was added to the mixture. The synthetic mixture has molar ratio of about 0.85 Na$_2$O/0.90 TPA Br/0.29 Al$_2$O$_3$/10 SiO$_2$/239 H$_2$O. The mixture was crystallized under agitation of 300 rpm at 150° C. for 80 hrs. The microspheres after the reaction were filtered from the mother liquor and then calcined at 600° C. for 2 hrs. The "as crystallized" microspheres were found to have 62% crystallinity by x-ray diffraction and a total BET surface area of 184 m$^2$/g. The air jet attrition rate (AJAR) was measured at 6.110 and attrition index of 43.68. The average crystal size measured by XRD is estimated ca. 932 Å.

Example 5

This example illustrates that the in-situ crystallization of ZSM-5 for the present disclosure can be accomplished in different temperatures.

The starting microspheres of this example were MS-1 as Example 1. The reaction mixture for in situ crystallization was composed of 6.84 g TPA Br, 107.6 g DI water, 3.22 g MetaMax®, 17.56 g seeds solution and 55 g MS-1. The reaction proceeded at about 160° C. under agitation of 300 rpm in an autoclave for 20 hours. The microspheres after the reaction were filtered from the mother liquor and then calcined at 600° C. for 2 hrs. The "as crystallized" microspheres were found to have 94% crystallinity by x-ray diffraction and a total BET surface area of 298.4 m$^2$/g. The air jet attrition rate (AJAR) was measured at 2.14 and attrition index of 22. The average crystal size measured by XRD is 501 Å.

Example 6

This example illustrates that the reactive mixture for in-situ crystallization of ZSM-5 for the present disclosure can be accomplished using different template compounds.

The starting microspheres of this example were MS-1 as described in Example 1. The reaction mixture for in-situ crystallization was composed of 17.1 g 40% TPA OH solution, 107.6 g DI water, 3.22 g MetaMax®, 17.56 g seeds solution and 55 g MS-1. The reaction proceeded at about 180° C. under agitation of 300 rpm in an autoclave for 20 hours. The microspheres after the reaction were filtered from the mother liquor and then calcined at 600° C. for 2 hrs. The "as crystallized" microspheres were found to have 92% crystallinity by x-ray diffraction and a total BET surface area of 320.7 m$^2$/g. The air jet attrition rate (AJAR) was measured at 1.95 and attrition index of 12.96. The average crystal size measured by XRD is 494 Å.

Example 7

This example illustrates that the reactive mixture for in-situ crystallization of ZSM-5 for the present disclosure can be accomplished without template compounds.

The starting microspheres of this example were MS-1 as described in Example 1. The reaction mixture for in-situ crystallization was composed of 107.6 g DI water, 3.22 g MetaMax®, 17.56 g seeds solution and 55 g MS-1. The reaction proceeded at about 180° C. under agitation of 300 rpm in an autoclave for 20 hours. The microspheres after the reaction were filtered from the mother liquor and then calcined at 600° C. for 2 hrs. The "as crystallized" microspheres were found to have 91% crystallinity by x-ray diffraction and a total BET surface area of 285.3 m$^2$/g. The air jet attrition rate (AJAR) was measured at 2.895 and attrition index of 17.52. The average crystal size measured by XRD is 776 Å.

Comparative Example 2

This comparative example illustrates that the reactive mixture for in-situ crystallization of ZSM-5 for the present disclosure may require at least an alkali metal compound.

The starting microspheres of this example were MS-1 as described in Example 1. The reaction mixture for in-situ crystallization was composed of 6.84 g TPA Br, 107.6 g DI water, 3.22 g MetaMax® and 55 g MS-1. The reaction proceeded at about 180° C. under agitation of 300 rpm in an autoclave for 20 hours. The microspheres after the reaction were filtered from the mother liquor and then calcined at 600° C. for 2 hrs. The "as crystallized" microspheres were found to have 55% crystallinity by x-ray diffraction and a total BET surface area of 185.9 m$^2$/g, indicating little or no in-situ ZSM-5 formation. The air jet attrition rate (AJAR) was measured at 4.725 and attrition index of 30.82. The average crystal size by XRD is estimated ca. 930 Å.

Example 8

This example illustrates that the ZSM-5 microsphere of the present disclosure can be made from other alkali compounds that replace the FCC seed solution used for crystallization in the previous Examples.

The starting microspheres of this example were MS-1 as Example 1. The reaction mixture for in-situ crystallization was composed of 108.1 g DI water, 6.84 g TPA Br, 3.39 g MetaMax®, 13.58 g N-brand, 4.82 g 50% NaOH solution and 55 g MS-1. The reaction proceeded at about 180° C. under agitation of 300 rpm in an autoclave for 20 hours. The microspheres after the reaction were filtered from the mother liquor and then calcined at 600° C. for 2 hrs. The "as crystallized" microspheres were found to have 94% crystallinity by x-ray diffraction and a total BET surface area of 315.9 m$^2$/g. The air j et attrition rate (AJAR) was measured at 2.84 and attrition index of 18.18. The average crystal size measured by XRD is 537 Å.

Example 9

This example illustrates that the ZSM-5 microsphere of the present disclosure can be made without seed solution used for crystallization or template compounds in the previous Examples.

The starting microspheres of this example were MS-1 as Example 1. The reaction mixture for in-situ crystallization was composed of 108.1 g DI water, 3.39 g MetaMax®, 9.64 g 50% NaOH solution and 55 g MS-1. The reaction proceeded at about 180° C. under agitation of 300 rpm in an autoclave for 20 hours. The microspheres after the reaction were filtered from the mother liquor and then calcined at 600° C. for 2 hrs. The "as crystallized" microspheres were found to have 93% crystallinity by x-ray diffraction and a total BET surface area of 317.6 m$^2$/g. The air jet attrition rate (AJAR) was measured at 2.475 and attrition index of 14.66. The average crystal size measured by XRD is 492 Å.

Example 10

This example illustrates that the in-situ crystallization of ZSM-5 for the present disclosure can be accomplished in different times.

The starting microspheres of this example were MS-1 as Example 1. The reaction mixture for in situ crystallization was composed of 6.84 g TPA Br, 107.6 g DI water, 3.22 g MetaMax®, 17.56 g seeds solution and 55.0 g MS-1. The reaction proceeded at about 180° C. under agitation of 300 rpm in an autoclave for 15 hours. The microspheres after the reaction were filtered from the mother liquor and then calcined at 600° C. for 2 hrs. The "as crystallized" microspheres were found to have 91% crystallinity by x-ray diffraction and a total BET surface area of 291.2 m$^2$/g. The average crystal size measured by XRD is 537 Å.

X-Ray Diffraction (XRD) of Examples 1-10

For XRD experiments, the samples were ground using a mortar and pestle and then packed back packed onto a flat plate mount for analysis. A PANalytical MPD X'Pert Pro diffraction system was used to collect data in Bragg-Brentano geometry. The Cu$_{K\alpha}$ radiation was used in the analysis with generator settings of 45 kV and 40 mA. The optical path consisted of a 1/8° divergence slit, 0.04 radian soller slits, 15 mm mask, 1/4° anti-scatter slit, 1/8° anti-scatter slit, 0.04 radian soller slits, Ni filter, and X'Celerator linear position sensitive detector. Data was collected from 30 to 70° 2θ using a step size of 0.017° 2θ and a count time of 60 s per step. Jade Plus 9 analytical X-ray diffraction software was used for phase identification. The phases present were identified by search/match of the PDF-4/Full File database from the International Center for Diffraction Data (ICDD). Crystallite size was obtained through Pawley refinement in Jade. Crystallinity data were collected using Topas.

Scanning Electron Microscopy (SEM) of Example 10

Figure 1:
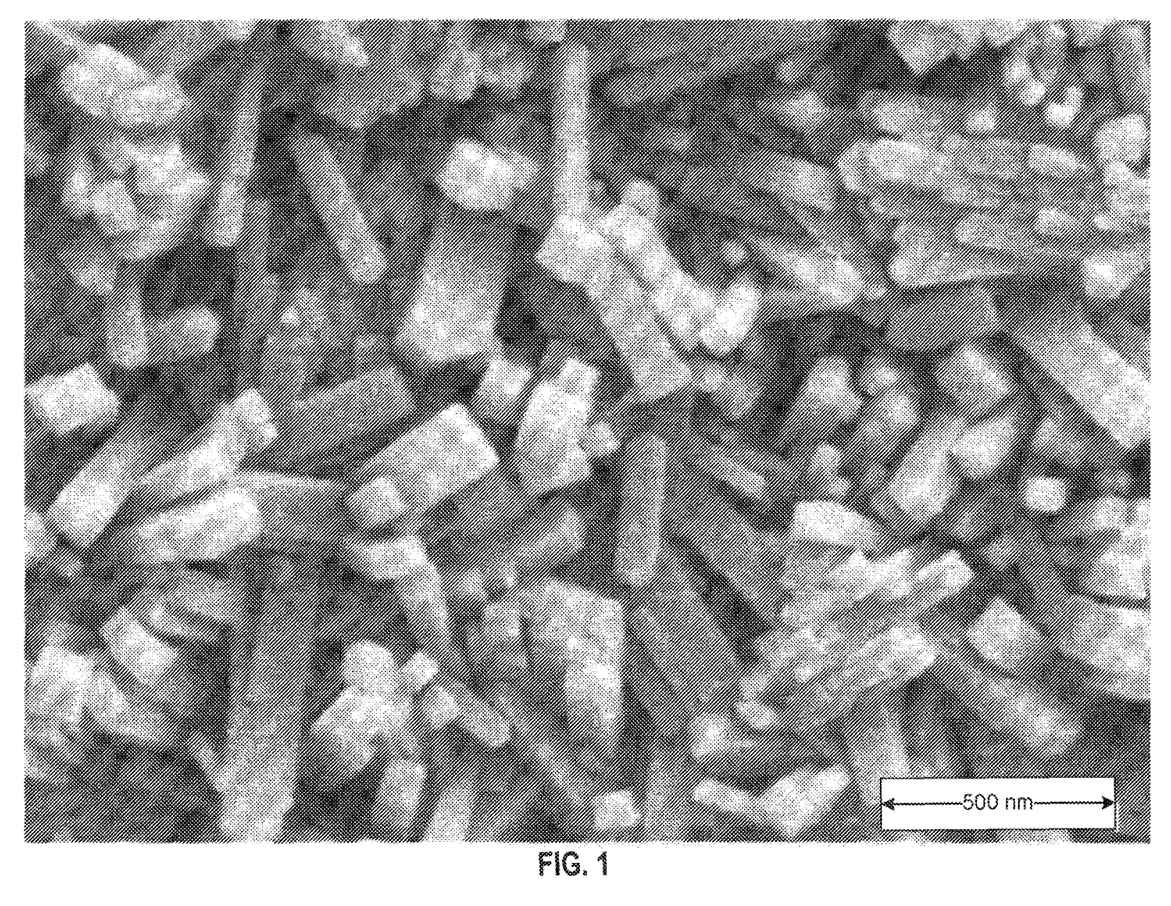
FIG. 1 illustrates a Scanning Electron Microscopy (SEM) picture of in-situ ZSM-5 zeolite microspheres.
Figure 2:
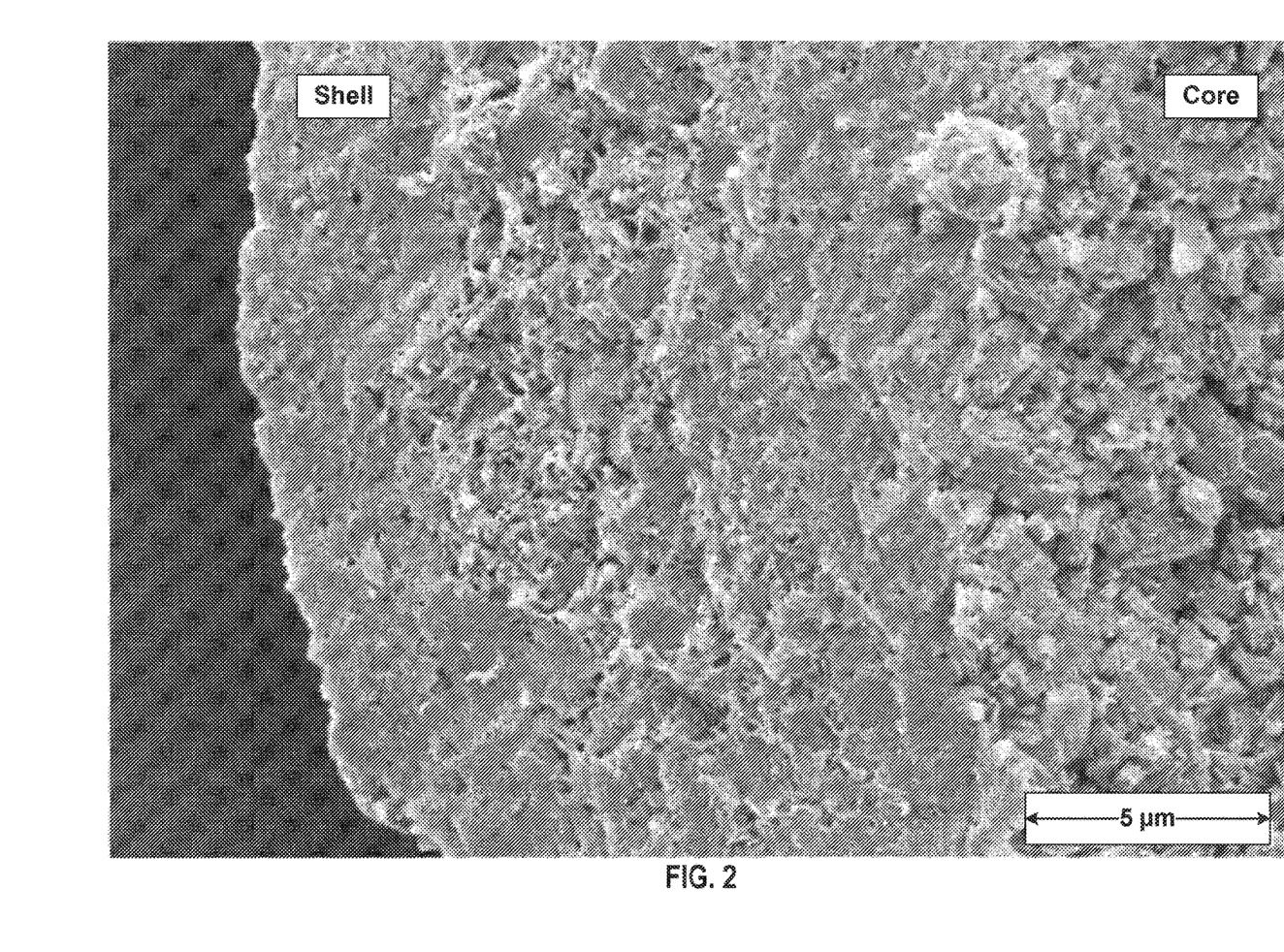
FIG. 2 illustrates a cross-section of an in-situ ZSM-5 zeolite microsphere.
Figure 3:
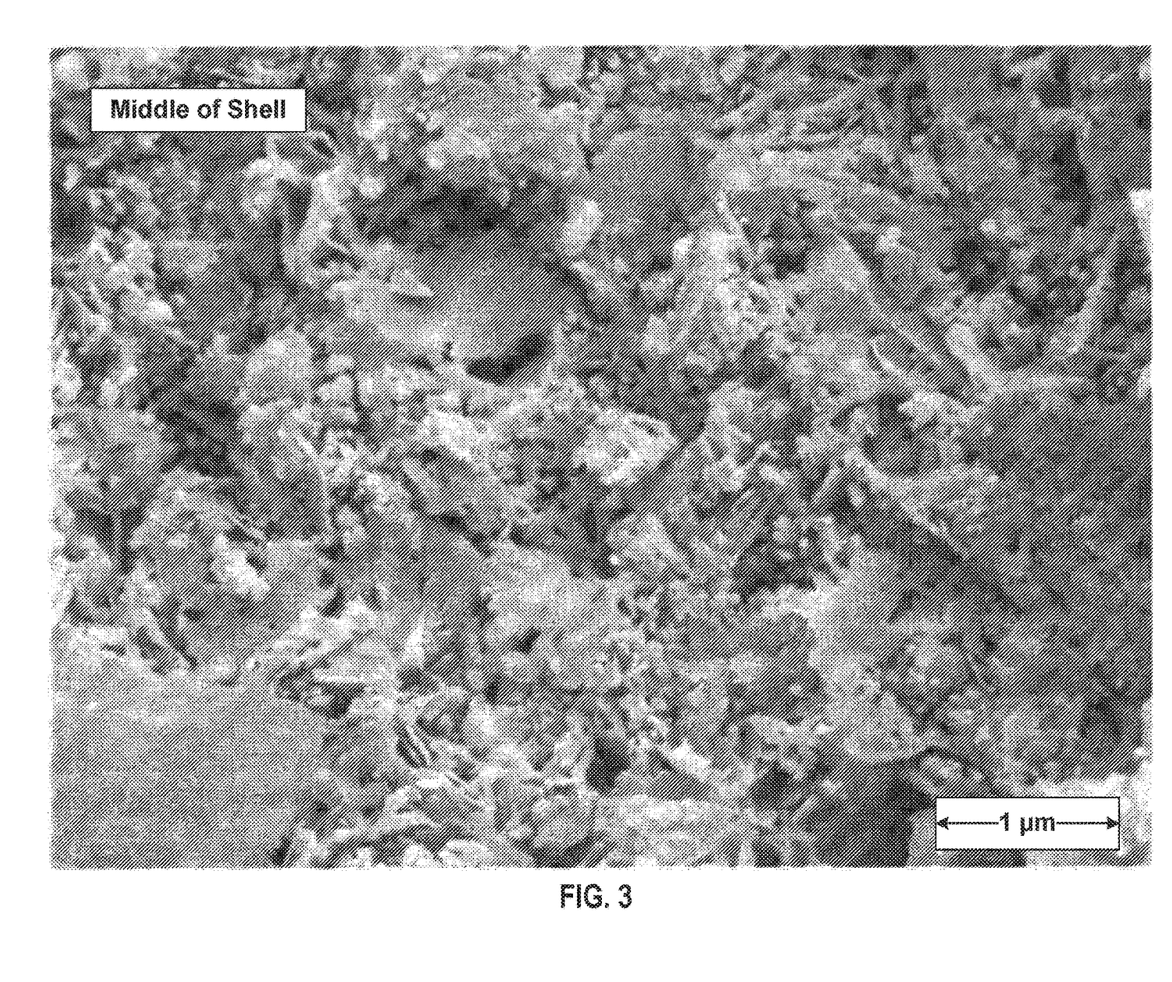
FIG. 3 illustrates a close-up SEM of the shell of an in-situ ZSM-5 zeolite microsphere.

The present disclosure of in-situ ZSM-5 crystallization process produces a material with crystalline and microsphere morphology. FIG. 1 shows the SEM picture of in-situ ZSM-5 zeolite-containing microsphere surface from Example 10. The surface is composed of inter-bound/intergrown, needle/coffin-shaped small ZSM-5 crystals to provide microsphere surface attrition resistance. FIG. 2 shows the SEM picture of part of a cleaved microsphere of Example 10 with shell and core exposed. FIG. 3 is the SEM picture of close examination of the shell morphology. These pictures demonstrate that this novel microsphere possesses a tightly bound ZSM-5 shell of at least 2 micron consisting of irregular, multi-crystalline, inter-bound/inter-grown small ZSM-5 crystals to provide excellent mechanical stability and physical integrity of the microspheres. The average crystal size as seen in FIG. 1 is about 550-350 Å.

In the foregoing description, numerous specific details are set forth, such as specific materials, dimensions, processes parameters, etc., to provide a thorough understanding of the embodiments of the present disclosure. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment, and such references mean "at least one".

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. ZSM-5 zeolite microspheres formed by 1) shaping a mixture into microspheres wherein the mixture comprises a silica material and a plurality of particulates selected from the group consisting of at least one high-density material with an absolute bulk density of at least 0.3 g/cc, ZSM-5 zeolite crystals, and combinations thereof; 2) calcining the microspheres; and 3) reacting and subsequently heating the microspheres with at least one alkali solution to form ZSM-5 zeolite in-situ on the microspheres, wherein the ZSM-5 zeolite microspheres contain substantially no clay or calcined clay material.

2. The ZSM-5 zeolite microspheres of claim 1, wherein the silica material is selected from the group consisting of colloid silica, silica sol, fumed silica, dense $SiO_2$ particles, precipitated silica, and amorphous silica doped with Al, and wherein the silica material is present in the amount of 20 to 95 wt. % of the mixture prior to the calcining the microspheres.

3. The ZSM-5 zeolite microspheres of claim 1, wherein the plurality of particulates comprises the at least one high-density material and the at least one high-density material is selected from the group consisting of $\alpha\text{-}Al_2O_3$, precipitated silica, steatite, minerals, silicates, aluminates, amorphous silica, and combinations thereof.

4. The ZSM-5 zeolite microspheres of claim 3, wherein the silica material coats the at least one high-density material to form a core-shell configuration prior to the calcining the microspheres, and wherein the at least one high-density material comprises $\alpha\text{-}Al_2O_3$.

5. The ZSM-5 zeolite microspheres of claim 3, wherein the at least one high-density material is present in the amount of 10 to 75 wt. % of the mixture prior to the calcining the microspheres, and wherein the calcining the microspheres is at 600 to 1000° C. for 2 to 4 hours.

6. The ZSM-5 zeolite microspheres of claim 1, wherein the shaping the mixture into microspheres further comprises adding water to the mixture to form an aqueous slurry and spray-drying the slurry, wherein the spray-drying is after the adding the water and before the calcining, and wherein the aqueous slurry further includes a spray-drying aid selected from the group consisting of ammonium citrate, sodium hexametaphosphate, ammonium tartrate, ammonium chloride, monoethylamine, ammonium oxalate, ammonium polyacrylate, carboxymethyl cellulose, polyvinyl alcohol, and tetrasodium phosphate.

7. The ZSM-5 zeolite microspheres of claim 1, wherein the alkali solution is a solution of at least one of zeolite Y seed, sodium silicate, sodium hydroxide, or ammonium hydroxide, wherein the reacting the microspheres with the at least one alkali solution produces a reactive mixture and the at least one alkali solution is present in the amount of 1 to 20 wt. % of the reactive mixture, and wherein the reacting and the subsequently heating the microspheres is with the at least one alkali solution and at least one organic template compound to form the ZSM-5 zeolite in-situ on the microspheres and the at least one organic template compound is selected from the group consisting of tetramethylammonium chloride, tetrapropylammonium bromide, tetrapropylammonium hydroxide, tri-n-propylamine, n-propyl bromide.

8. The ZSM-5 zeolite microspheres of claim 1, wherein the reacting and the subsequently heating the microspheres is with the at least one alkali solution and at least one organic template compound to form the ZSM-5 zeolite in-situ on the microspheres, the reacting the microspheres with the at least one alkali solution and the at least one organic template compound produces a reactive mixture, the at least one organic template compound is present in the amount of 1.5 to 15 wt. % of the reactive mixture, and no more than 8 wt. % of clay or calcined clay material is present in the mixture or in the ZSM-5 zeolite microspheres.

9. The ZSM-5 zeolite microspheres of claim 1, wherein the reacting and the subsequently heating the microspheres with at least one alkali solution to form ZSM-5 zeolite in-situ on the microspheres further includes adding an aluminum source selected from a group consisting of an aluminum salt, an aluminum hydroxide, aluminate, an aluminum oxide, and a metakaolin, wherein the reacting the microspheres with the at least one alkali solution and the adding the aluminum source produces a reactive mixture and the aluminum source is present in the amount of 0.1 to 3.0 wt. % of the reactive mixture, and wherein the reacting the microspheres with the at least one alkali solution produces a reactive mixture and the reactive mixture undergoes crystallization to form the ZSM-5 zeolite at a temperature from 140 to 200° C. for a period time from 5 hours to 100 hours.

10. The ZSM-5 zeolite microspheres of claim 1, wherein the ZSM-5 zeolite microspheres contain ZSM-5 crystals that have a crystal size of less than 800 angstroms, wherein the ZSM-5 zeolite microspheres have an air jet attrition rate (AJAR) of less than 4.0, and wherein the mixture contains substantially no ZSM-5 seeds.

11. The ZSM-5 zeolite microspheres of claim 1, wherein the reacting and the subsequently heating the microspheres further includes, after the calcining the microspheres, impregnating the microspheres with an organic template compound and after the impregnating, drying the microspheres prior to the reacting the microspheres, wherein the ZSM-5 zeolite microspheres have a size of between 25 to 200 microns, and wherein after the calcining and before the reacting, the microspheres have an absolute bulk density of at least 0.5 g/cc.

12. A method for forming ZSM-5 zeolite microspheres, the method comprising:
shaping a mixture into microspheres, wherein the mixture comprises a silica material and a plurality of particulates selected from the group consisting of at least one high-density material with an absolute bulk density of at least 0.3 g/cc, ZSM-5 zeolite crystals, and combinations thereof;
calcining the microspheres; and
reacting and subsequently heating the microspheres with at least one alkali solution to form ZSM-5 zeolite in-situ on the microspheres, wherein the ZSM-5 zeolite microspheres are substantially free of clay or calcined clay material.

13. The method of claim 12, wherein the silica material is selected from the group consisting of colloid silica, silica sol, fumed silica, dense $SiO_2$ particles, precipitated silica, and amorphous silica doped with Al, wherein the silica material is present in the amount of 20 to 95 wt. % of the mixture prior to the calcining the microspheres, wherein the plurality of particulates comprises the at least one high-density material and the at least one high-density material is selected from the group consisting of $\alpha\text{-}Al_2O_3$, precipitated silica, steatite, minerals, silicates, aluminates, amorphous silica, and combinations thereof, and wherein the silica material coats the at least one high-density material to form a core-shell configuration prior to the calcining the microspheres.

14. The method of any of claim 13, wherein the at least one high-density material is present in the amount of 10 to 75 wt. % of the mixture prior to the calcining the microspheres, wherein the calcining the microspheres is at 600 to 1000° C. for 2 to 4 hours, and wherein the at least one high-density material comprises $\alpha$-$Al_2O_3$.

15. The method of claim 12, wherein the shaping the mixture into microspheres further comprises adding water to the mixture to form an aqueous slurry and spray-drying the slurry, wherein the spray-drying is after the adding the water and before the calcining, wherein the aqueous slurry further includes a spray-drying aid selected from the group consisting of ammonium citrate, sodium hexametaphosphate, ammonium tartrate, ammonium chloride, monoethylamine, ammonium oxalate, ammonium polyacrylate, carboxymethyl cellulose, polyvinyl alcohol, and tetrasodium phosphate, and wherein the alkali solution is a solution of at least one of zeolite Y seed, sodium silicate, sodium hydroxide, or ammonium hydroxide.

16. The method of claim 12, wherein the reacting the microspheres with the at least one alkali solution produces a reactive mixture and the at least one alkali solution is present in the amount of 1 to 20 wt. % of the reactive mixture, wherein the reacting and the subsequently heating the microspheres is with the at least one alkali solution and at least one organic template compound to form the ZSM-5 zeolite in-situ on the microspheres and the at least one organic template compound is selected from the group consisting of tetramethylammonium chloride, tetrapropylammonium bromide, tetrapropylammonium hydroxide, tri-n-propylamine, n-propyl bromide.

17. The method of claim 12, wherein
the reacting and the subsequently heating the microspheres is with the at least one alkali solution and at least one organic template compound to form the ZSM-5 zeolite in-situ on the microspheres,
the reacting the microspheres with the at least one alkali solution and the at least one organic template compound produces a reactive mixture,
the at least one organic template compound is present in the amount of 1.5 to 15 wt. % of the reactive mixture, and
no more than 8 wt. % of clay or calcined clay material is present in the mixture or in the ZSM-5 zeolite microspheres.

18. The method of claim 12, wherein the reacting and the subsequently heating the microspheres with at least one alkali solution to form ZSM-5 zeolite in-situ on the microspheres further includes adding an aluminum source selected from a group consisting of an aluminum salt, an aluminum hydroxide, aluminate, an aluminum oxide, and a metakaolin, wherein the reacting the microspheres with the at least one alkali solution and the adding the aluminum source produces a reactive mixture and the aluminum source is present in the amount of 0.1 to 3.0 wt. % of the reactive mixture, and wherein the reacting the microspheres with the at least one alkali solution produces a reactive mixture and the reactive mixture undergoes crystallization to form the ZSM-5 zeolite at a temperature from 140 to 200° C. for a period time from 5 hours to 100 hours.

19. The method of claim 12, wherein the ZSM-5 zeolite microspheres contain ZSM-5 crystals that have a crystal size of less than 800 angstroms, wherein the ZSM-5 zeolite microspheres have an air jet attrition rate (AJAR) of less than 4.0, and wherein the mixture contains substantially no ZSM-5 seeds.

20. The method of any of claim 12, wherein the reacting and the subsequently heating the microspheres further includes, after the calcining the microspheres, impregnating the microspheres with an organic template compound and after the impregnating, drying the microspheres prior to the reacting the microspheres, wherein the microspheres have a size of between 25 to 200 microns, and wherein after the calcining and before the reacting, the microspheres have an absolute bulk density of at least 0.5 g/cc.

* * * * *